(12) United States Patent
Daniel et al.

(10) Patent No.: US 8,058,237 B2
(45) Date of Patent: Nov. 15, 2011

(54) STABLE COMPOSITION OF GDF-5 AND METHOD OF STORAGE

(75) Inventors: Peter Daniel, Natick, MA (US); Asok C. Sen, Norwood, MA (US); Dongling Su, Franklin, MA (US)

(73) Assignee: Advanced Technologies & Regenerative Medicine, LLC

( * ) Notice: Subject to any disclaimer, the term of this patent is extended or adjusted under 35 U.S.C. 154(b) by 297 days.

(21) Appl. No.: 12/174,168

(22) Filed: Jul. 16, 2008

(65) Prior Publication Data

US 2009/0043078 A1 Feb. 12, 2009

Related U.S. Application Data

(60) Provisional application No. 60/954,413, filed on Aug. 7, 2007.

(51) Int. Cl.
*A61K 38/18* (2006.01)
*A61K 38/16* (2006.01)
*C07K 14/00* (2006.01)

(52) U.S. Cl. .................. 514/8.8; 514/21.2; 530/350

(58) Field of Classification Search .................. None
See application file for complete search history.

(56) References Cited

U.S. PATENT DOCUMENTS

| | | |
|---|---|---|
| 2,931,802 A | 4/1960 | Touey |
| 4,120,810 A | 10/1978 | Palmer |
| 4,891,319 A | 1/1990 | Roser |
| 5,011,691 A | 4/1991 | Oppermann |
| 5,013,649 A | 5/1991 | Wang |
| 5,202,311 A | 4/1993 | Folkman |
| 5,231,169 A | 7/1993 | Constantz |
| 5,266,683 A | 11/1993 | Oppermann |
| 5,318,898 A | 6/1994 | Israel |
| 5,385,887 A | 1/1995 | Yim |
| 5,411,941 A | 5/1995 | Grinna |
| 5,455,231 A | 10/1995 | Constantz |
| 5,516,654 A | 5/1996 | Israel |
| 5,658,882 A | 8/1997 | Celeste |
| 5,747,058 A | 5/1998 | Tipton |
| 5,770,700 A | 6/1998 | Webb |
| 5,776,193 A | 7/1998 | Kwan |
| 5,801,014 A | 9/1998 | Lee |
| 5,804,557 A | 9/1998 | Cleland |
| 5,866,165 A | 2/1999 | Liu |
| 5,955,448 A | 9/1999 | Colaco |
| 5,968,542 A | 10/1999 | Tipton |
| 5,972,385 A | 10/1999 | Liu |
| 5,985,320 A | 11/1999 | Edwards |
| 6,051,558 A | 4/2000 | Burns |
| 6,071,428 A | 6/2000 | Franks |
| 6,165,981 A | 12/2000 | Flaa |
| 6,171,584 B1 | 1/2001 | Hotten et al. |
| 6,171,586 B1 | 1/2001 | Lam |
| 6,187,742 B1 | 2/2001 | Wozney |
| 6,207,718 B1 | 3/2001 | Papadimitriou |
| 6,281,195 B1 | 8/2001 | Rueger |
| 6,284,872 B1 | 9/2001 | Celeste |
| 6,288,043 B1 | 9/2001 | Spiro |
| 6,340,369 B1 | 1/2002 | Ferree |
| 6,344,058 B1 | 2/2002 | Ferree |
| 6,352,557 B1 | 3/2002 | Ferree |
| 6,407,060 B1 | 6/2002 | Charette |
| 6,419,702 B1 | 7/2002 | Ferree |
| 6,454,804 B1 | 9/2002 | Ferree |
| 6,551,801 B1 | 4/2003 | Andou |
| 6,645,247 B2 | 11/2003 | Ferree |
| 6,648,918 B2 | 11/2003 | Ferree |
| 6,648,919 B2 | 11/2003 | Ferree |
| 6,648,920 B2 | 11/2003 | Ferree |
| 6,656,492 B2 | 12/2003 | Kajiyama |
| RE38,385 E | 1/2004 | Franks et al. |
| 6,685,695 B2 | 2/2004 | Ferree |
| 6,719,968 B2 | 4/2004 | Celeste |
| 6,723,170 B2 | 4/2004 | Ohashi |
| 6,755,863 B2 | 6/2004 | Ferree |
| 6,764,994 B1 | 7/2004 | Hötten |
| 6,780,324 B2 | 8/2004 | Le Garrec |
| 6,911,411 B2 | 6/2005 | Cox |
| 6,936,582 B1 | 8/2005 | Charette |
| 6,991,790 B1 | 1/2006 | Lam |
| 6,992,065 B2 | 1/2006 | Okumu |
| 7,060,268 B2 | 6/2006 | Andya |
| RE39,497 E | 2/2007 | Kono et al. |
| 7,235,527 B2 | 6/2007 | Makishima |
| 7,318,840 B2 | 1/2008 | McKay |
| 7,323,445 B2 | 1/2008 | Zhang |

(Continued)

FOREIGN PATENT DOCUMENTS

EP 955313 A1 11/1999

(Continued)

OTHER PUBLICATIONS

Letter from Keith E. Gilman of Lerner David Littenberg Krumholz & Mentlik LLP, dated Sep. 13, 2010 regarding Johnson & Johnson U.S. Publication No. 2008/0147077A1.

(Continued)

*Primary Examiner* — Elly-Gerald Stoica

(57) ABSTRACT

Improved compositions and methods are provided for stabilizing a solution of bone morphogenetic protein. The compositions comprise an aqueous solution of GDF-5 and a biocompatible acid, such as hydrochloric, acetic, phosphoric, or trifluoroacetic acid, wherein the solution has a pH of from about 3.0 to about 3.6, thereby providing for improved stability of the GDF-5 protein during handling and prolonged storage at reduced temperatures.

6 Claims, 17 Drawing Sheets

U.S. PATENT DOCUMENTS

| | | |
|---|---|---|
| 7,375,077 B2 | 5/2008 | Mao |
| 7,435,260 B2 | 10/2008 | Ferree |
| 7,572,440 B2 | 8/2009 | Vukicevic |
| 7,678,764 B2 | 3/2010 | Garigapati |
| 2001/0024823 A1 | 9/2001 | Vukicevic |
| 2002/0032155 A1 | 3/2002 | Ferree |
| 2002/0128718 A1 | 9/2002 | Ferree |
| 2002/0165542 A1 | 11/2002 | Ferree |
| 2002/0173770 A1 | 11/2002 | Flory |
| 2003/0026788 A1 | 2/2003 | Ferree |
| 2003/0185812 A1 | 10/2003 | Ferree |
| 2003/0192554 A1 | 10/2003 | Ferree |
| 2004/0022771 A1 | 2/2004 | Ferree |
| 2004/0024471 A1 | 2/2004 | Ferree |
| 2004/0028733 A1 | 2/2004 | Tracy |
| 2004/0132653 A1 | 7/2004 | Ichikawa |
| 2004/0146923 A1 | 7/2004 | Celeste |
| 2004/0197324 A1 | 10/2004 | Liu |
| 2005/0069571 A1 | 3/2005 | Slivka |
| 2005/0119754 A1 | 6/2005 | Trieu |
| 2005/0191248 A1 | 9/2005 | Hunter |
| 2006/0024346 A1 | 2/2006 | Brody |
| 2006/0088565 A1 | 4/2006 | Kohnert |
| 2006/0121113 A1 | 6/2006 | Bartholomaeus |
| 2006/0223120 A1 | 10/2006 | Kim |
| 2006/0286171 A1 | 12/2006 | Zhou |
| 2006/0286289 A1 | 12/2006 | Prajapati |
| 2006/0287676 A1 | 12/2006 | Prajapati |
| 2007/0053871 A1 | 3/2007 | Li |
| 2007/0098756 A1 | 5/2007 | Behnam |
| 2007/0172479 A1 | 7/2007 | Warne |
| 2007/0178159 A1 | 8/2007 | Chen |
| 2008/0098614 A1 | 5/2008 | Tchessalov |
| 2008/0147077 A1 | 6/2008 | Garigapati |
| 2008/0234727 A1 | 9/2008 | Garigapati |
| 2008/0311078 A1 | 12/2008 | Gokarn |
| 2009/0004048 A1 | 1/2009 | Elliott |
| 2009/0030483 A1 | 1/2009 | Risi |
| 2009/0043078 A1 | 2/2009 | Daniel |
| 2009/0048412 A1 | 2/2009 | Soula |
| 2009/0060976 A1 | 3/2009 | Rueger |
| 2009/0099089 A1 | 4/2009 | Zhang |
| 2009/0259023 A1 | 10/2009 | Su |
| 2009/0286764 A1 | 11/2009 | Kipp |
| 2009/0291062 A1 | 11/2009 | Fraunhofer |
| 2010/0015230 A1 | 1/2010 | Ron |
| 2010/0041870 A1 | 2/2010 | Tchessalov |
| 2010/0130730 A1 | 5/2010 | Garigapati |
| 2010/0144631 A1 | 6/2010 | Ron |
| 2010/0255100 A1 | 10/2010 | Margolin |

FOREIGN PATENT DOCUMENTS

| | | |
|---|---|---|
| EP | 957943 B1 | 5/2003 |
| EP | 1350525 A2 | 10/2003 |
| EP | 1448246 A1 | 8/2004 |
| EP | 1462126 A1 | 9/2004 |
| EP | 1274459 B1 | 11/2005 |
| EP | 1604693 A1 | 12/2005 |
| EP | 1604963 A2 | 12/2005 |
| EP | 955313 B1 | 5/2006 |
| EP | 1915986 A1 | 4/2008 |
| EP | 1932519 | 6/2008 |
| EP | 957943 B2 | 11/2008 |
| WO | WO 8800205 A1 | 1/1988 |
| WO | WO 9011366 A1 | 10/1990 |
| WO | WO 9118098 A1 | 11/1991 |
| WO | WO 9200382 A1 | 1/1992 |
| WO | WO 9309229 A1 | 5/1993 |
| WO | WO 9316099 A2 | 8/1993 |
| WO | WO 9410203 A2 | 5/1994 |
| WO | WO 9415949 A1 | 7/1994 |
| WO | WO 9415965 A1 | 7/1994 |
| WO | WO 9415966 A1 | 7/1994 |
| WO | WO 9421681 A1 | 9/1994 |
| WO | WO 9426892 A1 | 11/1994 |
| WO | WO 9426893 A1 | 11/1994 |
| WO | WO 9501801 A1 | 1/1995 |
| WO | WO9504819 A1 | 2/1995 |
| WO | WO 9510539 A1 | 4/1995 |
| WO | WO 9510802 A1 | 4/1995 |
| WO | WO 9516035 A2 | 6/1995 |
| WO | WO 9533830 A1 | 12/1995 |
| WO | WO 9601316 A1 | 1/1996 |
| WO | WO 9601845 A1 | 1/1996 |
| WO | WO9614335 A1 | 5/1996 |
| WO | WO 9636710 A1 | 11/1996 |
| WO | WO0178683 A2 | 10/2001 |
| WO | WO 03000282 A1 | 1/2003 |
| WO | WO 03030923 A1 | 4/2003 |
| WO | WO 03/043673 | 5/2003 |
| WO | WO 03043673 A1 | 5/2003 |
| WO | WO 03066120 A1 | 8/2003 |
| WO | WO 2004037265 A1 | 5/2004 |
| WO | WO 2004052336 A2 | 6/2004 |
| WO | WO 2005060989 A1 | 7/2005 |
| WO | WO 2005100399 A2 | 10/2005 |
| WO | WO 2005107765 A2 | 11/2005 |
| WO | WO 2005115438 A1 | 12/2005 |
| WO | WO 2006/138099 | 12/2006 |
| WO | WO 2006138099 A2 | 12/2006 |
| WO | WO 2006138181 A2 | 12/2006 |
| WO | WO 2007025441 A1 | 3/2007 |
| WO | WO 2008009419 A1 | 1/2008 |
| WO | WO 2008045498 A1 | 4/2008 |
| WO | WO 2008049588 A1 | 5/2008 |
| WO | WO 2008079672 A2 | 7/2008 |
| WO | WO 2008082563 A2 | 7/2008 |
| WO | WO 2008099190 A2 | 8/2008 |
| WO | WO 2008099198 A2 | 8/2008 |
| WO | WO 2008143867 A1 | 11/2008 |
| WO | WO 2009006097 A1 | 1/2009 |
| WO | WO 2009006301 A2 | 1/2009 |
| WO | WO 2009015736 A1 | 2/2009 |
| WO | WO 2009016131 A1 | 2/2009 |
| WO | WO 2009016333 A1 | 2/2009 |
| WO | WO 2009020744 A1 | 2/2009 |

OTHER PUBLICATIONS

EP Search Report 07254571.8, May 8, 2008.

EP Search Report for App. No. PCT/US2009/039925 dated Aug. 10, 2009.

Arakawa et al., Pharmaceutical Research "Protein-Solvent Interactions in Pharmaceutical Formulations", vol. 8, No. 3, 1991, pp. 285-291.

Brus, C. et. al., "Stabilization of Oligonucleotide-Polyethylenimine Complexes by Freeze-Drying: Physicochemical and Biological Characterization". Journal of Controlled Release, Feb. 20, 2004, vol. 95, Issue 1, pp. 119-131.

Cheng, Hongwei. "Osteogenic Activity of the Fourteen Types of Human Bone Morphogenic Proteins", Journal Bone Joint Surgery Am. 85A, 2003, pp. 1544-1552.

Costantino, Henry R. et. al., "Effect of Excipients on the Stability and Structure of Lyophilized Recombinant Human Growth Hormone", Journal of Pharmaceutical Sciences, 1998, vol. 87, Issue 11, pp. 1412-1420.

Crowe, J., "Stabilization of Dry Phospholipid Bilayers and Proteins by Sugars", Biochem. J., 1987, 242, pp. 1-10.

Gloger, O., "Lyoprotection of Aviscumine with Low Molecular Weight Dextrans", International Journal of Pharmaceutics, Jul. 9, 2003, vol. 260, Issue 1, pp. 59-68.

Goodnough, M C, et. al., "Stabilization of Botulinum Toxin Type A During Lyophilization", Applied Environmental Microbiology, 1992, vol. 58, Issue 10, pp. 3426-3428.

Gupta Intl J Pharm 318 (2006) 163-173.

Honda et al. Jouranl of Bioscience and Bioengineering 89(6), 582-589 (2000).

Lories, Rik, J. U., "Bone Morphogenetic Protein Signaling in Joint Homeostasis and Disease", Cytokine Growth Factor Review, vol. 16, Issue 3, 2005, pp. 287-298.

Lyons, K et. al., "Vgr-1, a Mammalian Gene Related to Xenopus Vg-1, is a M Member of the Transforming Growth Factor Beta Gene Superfamily", Proceedings of the National Academy of Science, 1989, vol. 86, Issue 12, pp. 4554-4558.

Massague, J., "The Transforming Growth Factor-beta Family", Annual Review of Cell Biology, Nov. 1990, vol. 6, pp. 597-641.

Ozkaynak et. al., "OP-1 cDNA Encodes an Osteogenic Protein in the TGF-Beta Family". EMBO Journal, 1990, vol. 9, Issue 7, pp. 2085-2093.

Ramos et. al., "Stabilization of Enzymes Against Thermal Stress and Freeze-Drying by Mannosylglycerate", Appl. Envir. Microiol. 1997, vol. 63, Issue 10, pp. 4020-4025.

Ruppert, et al. Eur J Biochem 237, 295-302 (1996).

Wharton, KA et. al., "Drosophila 60A Gene, Another Transforming Growth Factor Beta Family Member, is Closely Related to Human Bone Morphogenetic Proteins", Proceedings of the National Academy of Science, 1991, vol. 88, Issue 20, pp. 9214-9218.

Yancey, Paul, "Organic Osmolytes as Compatible, Metabolic and Counteracting Cytoprotectants in High Osmolarity and Other Stresses" Journal of Experimental Biology, 2005, vol. 208, pp. 2819-2830.

Von Heijne, Nucleic Acids Research 14:4683-4691 (1986).

Rickert et al., Growth Factors, 19, 2001, 115-123.

Schmidmaier, J. Biomedical Materials Res Appl Biomat, 58, 449-455, 2001.

Rothenberger, Surgical Infection Society Journal Supp, Dec. 2002, p. 579-87.

Mangram, Infection control and Hospital Epidemiology, 1999, 20(40, 247-280).

Lee et al., Proc. Natl. Acad. Sci 88:4250-4254 1991.

Mazzocca AAOS Abstract #338 2005.

Wright 50th ORS #1234 2004.

Peterson 51st ORS #0076 2005.

Arakawa et al., Factors affecting short-term and long-term stabilities of protein, Advanced Drug Delivery Reviews, 2001, pp. 307-326, vol. 46.

Basler et al., Control of Cell Pattern in the Neural Tube: Regulation of Cell Differentiation by dorsalin-1, a Novel TGFβFamily Member, Cell, 1993, 687-702, 73.

Celeste, AJ et. al., "Identification of Transforming Growth Factor Beta Family Members Present in Bone-Inductive Protein Purified from Bovine Bone", Proceedings of the National Academy of Science, 1990, pp. 9843-9847, vol. 87, Issue 24.

Crowe, J., "The Trehalose Myth Revisited: Introduction to a Symposium on Stabilization of Cells in the Dry State", Cryobiology, Sep. 2001, pp. 89-105, vol. 43, Issue 2.

Dayhoffel et al., A Model of Evolutionary Change in Proteins, Atlas of Protein Sequence and Structure, 1978, pp. 354-352, vol. Suppl 3.

Higashiyama et al., Novel functions and applications of trehalise, Pure Appl. Chem. 2002, pp. 1263-1269, vol. 74, No. 7.

Nakamoto et al., The small heat shock proteins and their clients, Cell. Mol. Life Sci, 2007, pp. 294-306, vol. 64.

Needleman et al., A General Method Applicable to the Search for Similarities in the Amino Acid Sequence of Two Proteins, J. Mol. Biol. 1970, 443-453, vol. 48.

Padgett et al., A transcript from a Drosophila pattern gene predicts a protein homologous to the transforming growth factor-B family, Nature 1987, 81-84, vol. 325.

Wozney et al., Novel Regulators of Bone Formation: Molecular Clones and Activities, Science 1988, 1528-1534, vol. 242.

Sampath, T.K., "Bovine Osteogenic Protein is Composed of Dimers of OP-1 and BMP-2A, Two Members of the Transorming Frowth Factor-Beta Superfamily", J Biol Chem, 1990, pp. 13198-13205, vol. 265, Issue 22.

Storm et al., Limb alterations in brachypodism mice due to mutations in a new member of the TGFβ-superfamily, Nature 1994, 639-643, vol. 368.

Takao et al., Identification of Rate Bone Morphogenetic Protein-3b (BMP-3b), a New Member of BMP-3, Biochemical and Biophysical Research Communications, 1996, 656-662, vol. 219.

Triantfilou et al., A CD14-independent LPS receptor cluster, Nature Immunology 2001, 338-345, vol. 2.

Wang et al., Instability, stabilization, and formulation of liquid protein pharmaceuticals, International Journal of Pharmaceutics, 1999, pp. 129-188, vol. 185.

Weeks, A Maternal mRNA Localized to the Vegetal Hemisphere in Zenopus Eggs Codes for a Growth Factor Related to TGF-β, Cell, 1987, 8614-867, vol. 51.

PCT Search Report dated Jul. 10, 2008 for application No. PCT/US2008/068007.

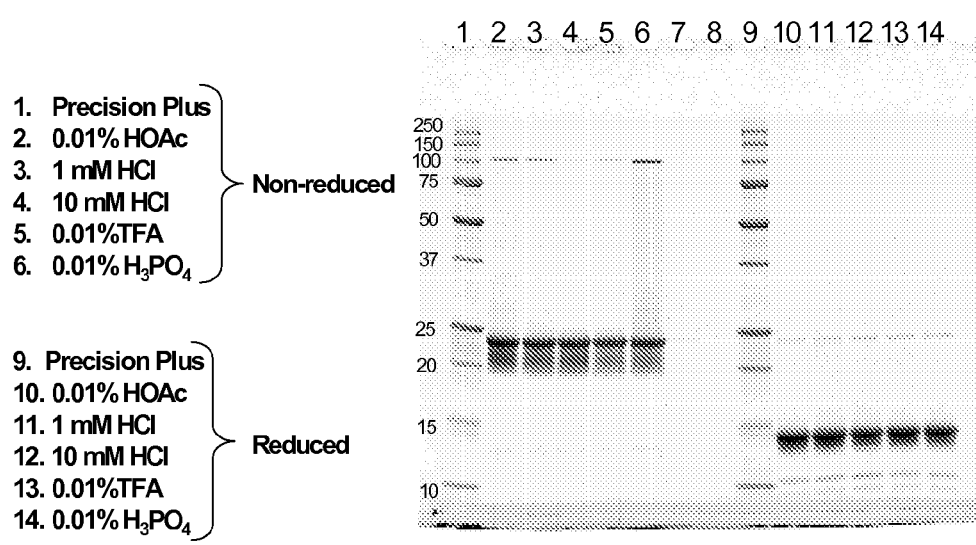
Fig. 1: SDS-PAGE analysis of various reduced and non-reduced GDF-5 compositions.

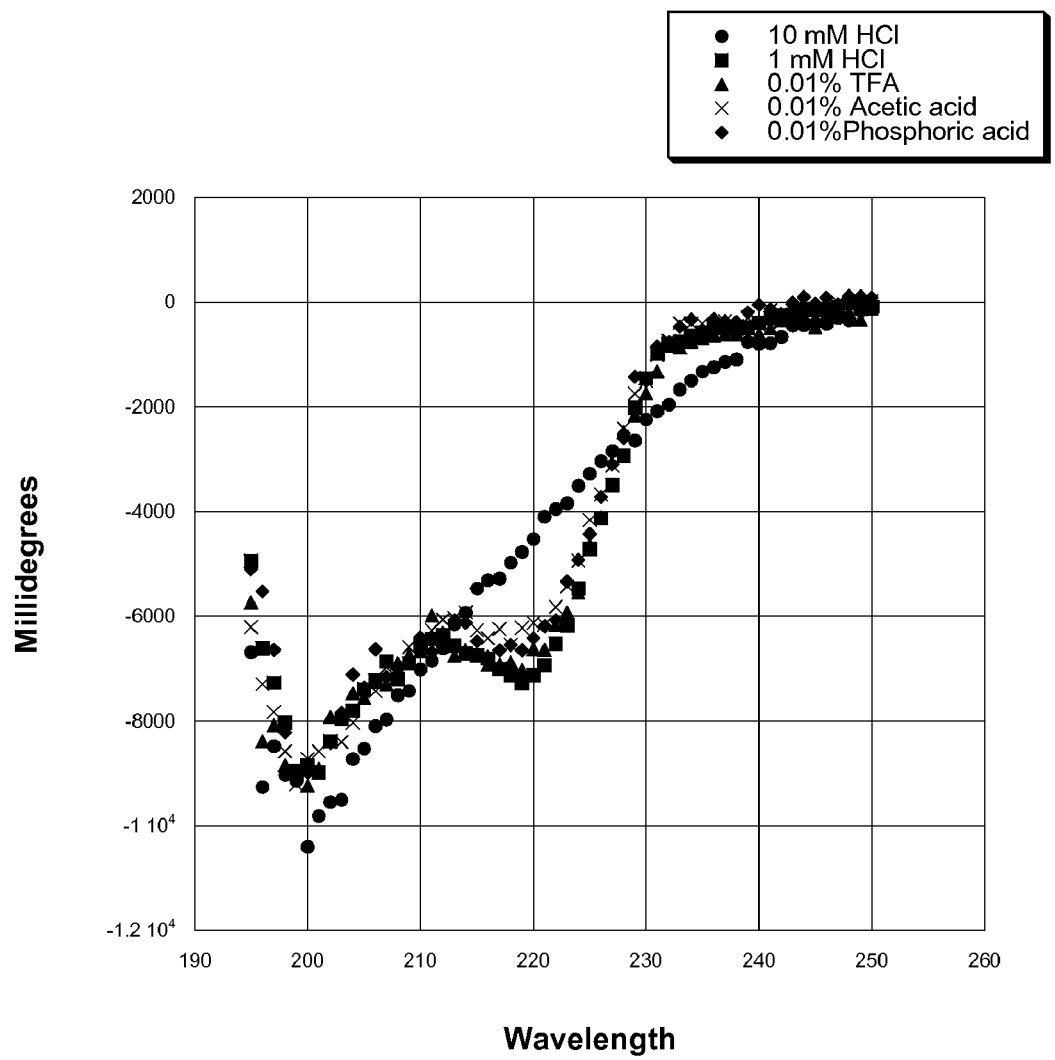
Fig. 2: Circular Dichroism analysis of various GDF-5 compositions.

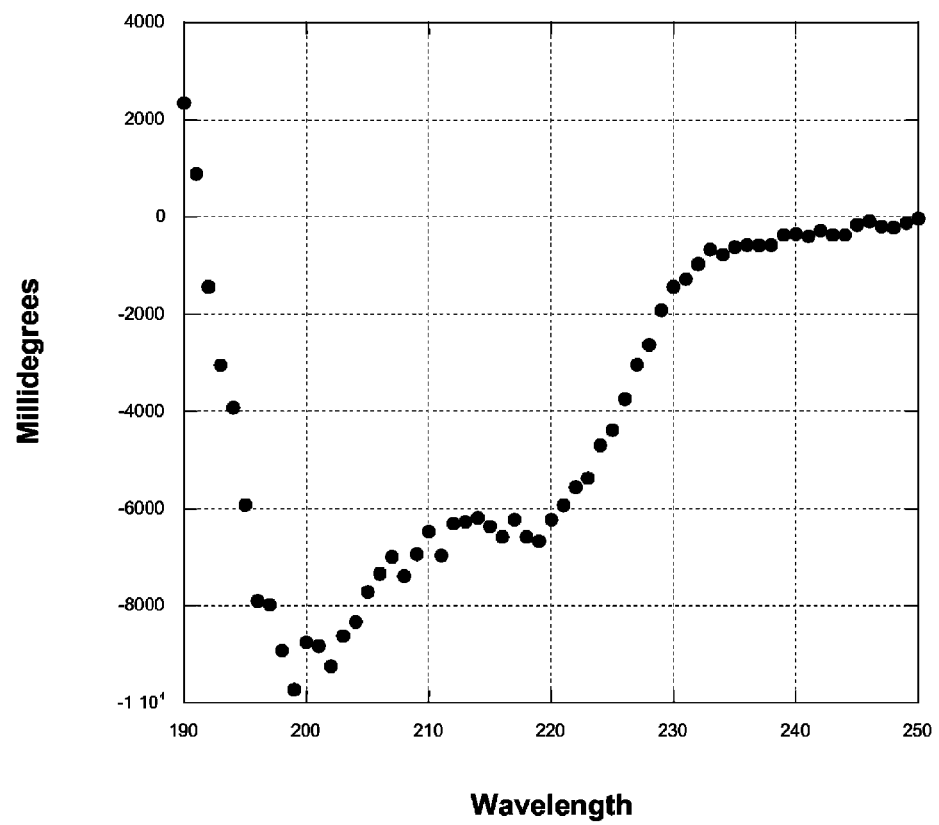
Fig. 3: Circular Dichroism analysis of a stock 10 mM HCl GDF-5 solution further diluted with water). Water was used as a blank.

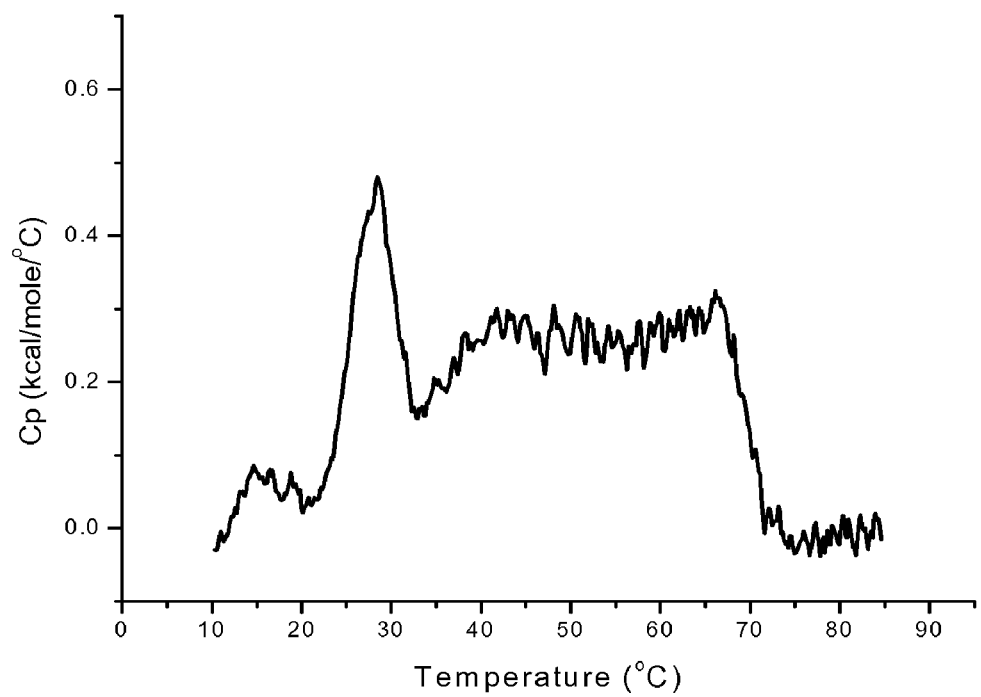
Fig. 4a: DSC spectra of GDF-5 in 10 mM HCl

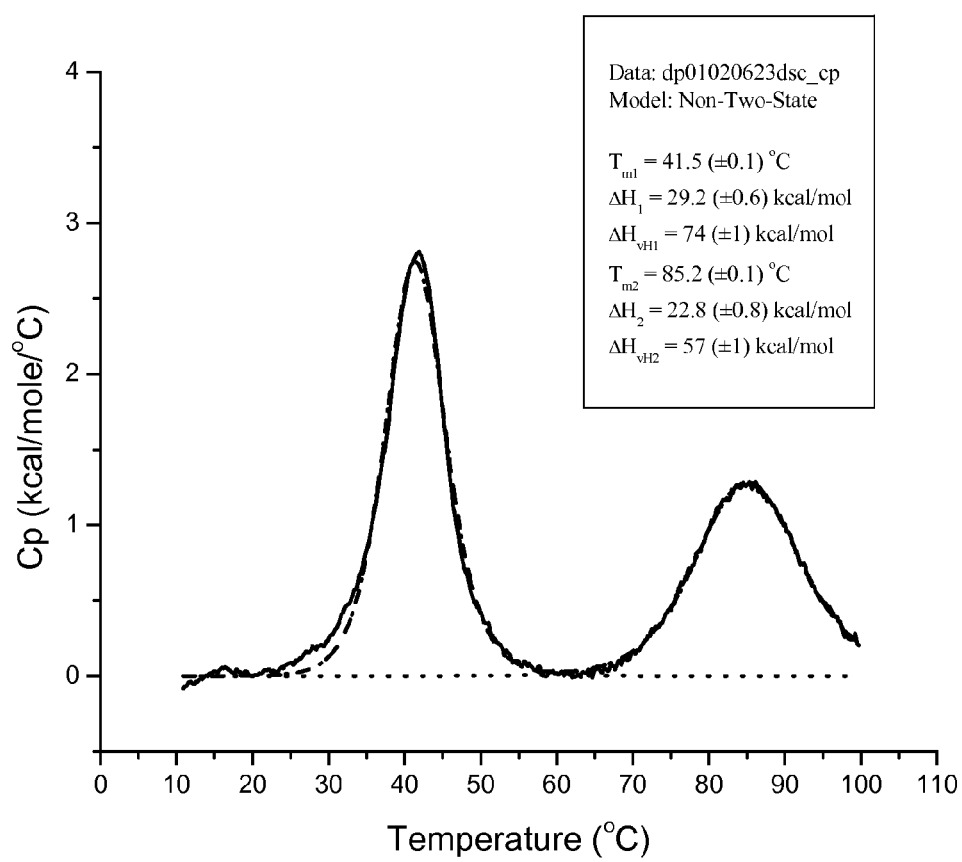
Fig. 4b: DSC spectra of GDF-5 in 1 mM HCl.

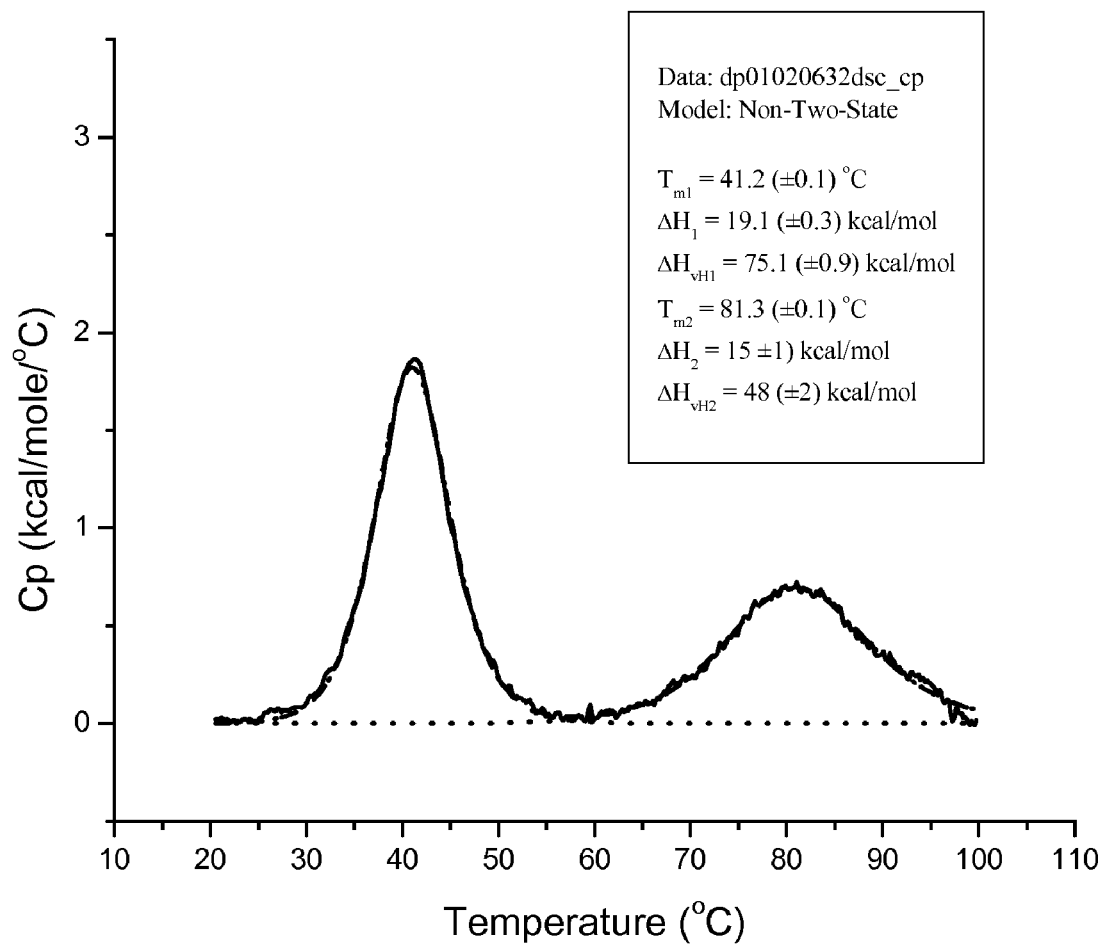
Fig. 4c: DSC spectra of GDF-5 in 0.01% (v/v) TFA.

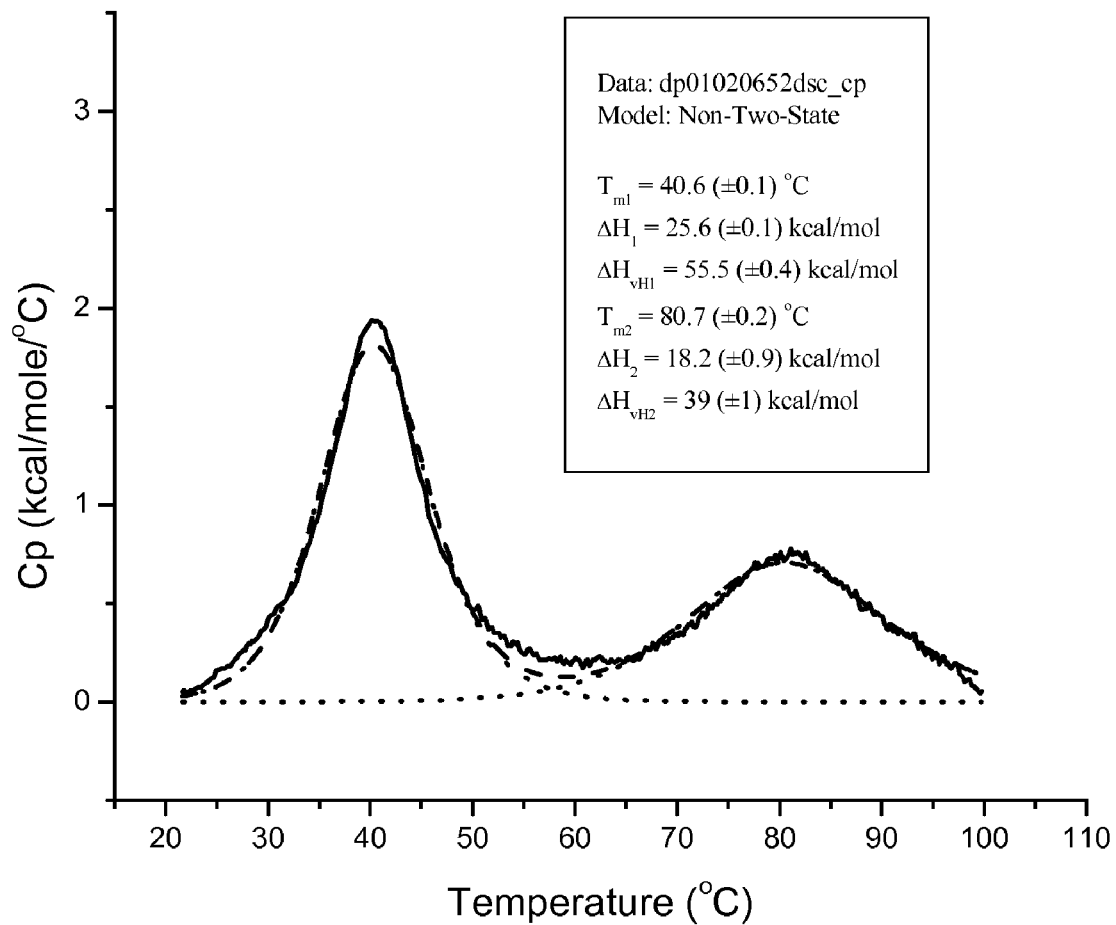
Fig. 4d: DSC spectra of GDF-5 in 0.01% (v/v) phosphoric acid.

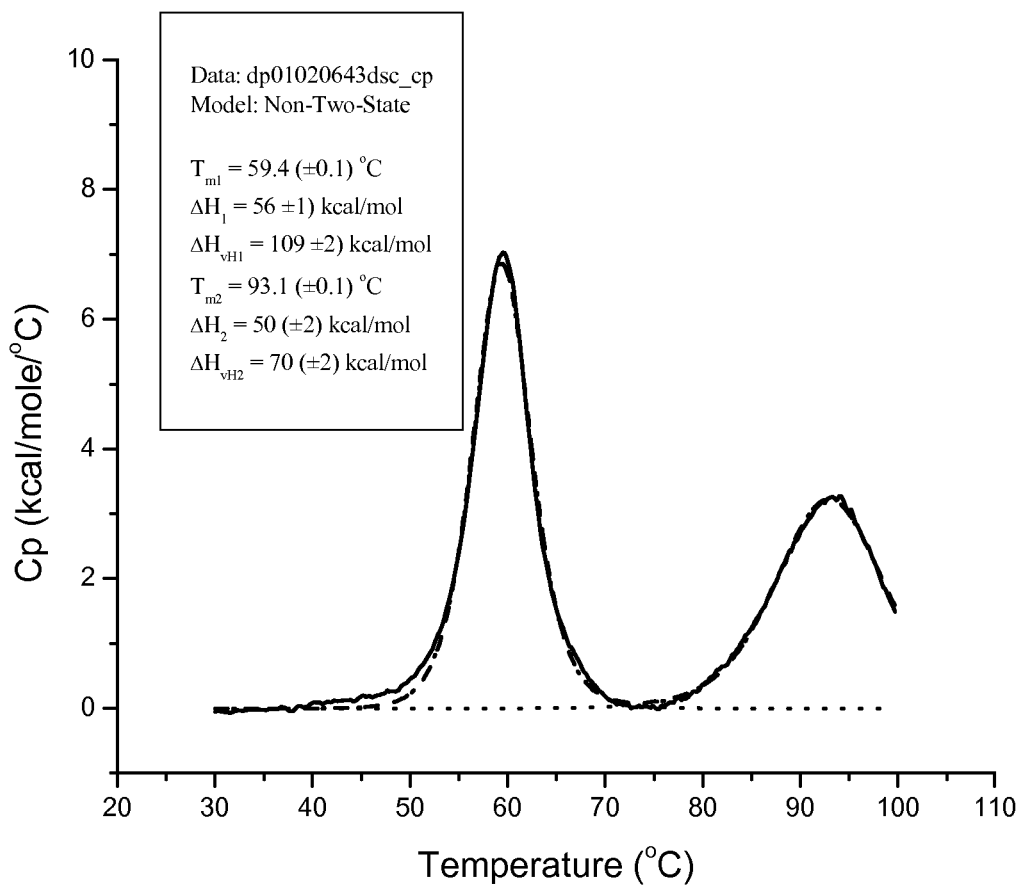
Fig. 4e: DSC spectra of GDF-5 in 0.01% (v/v) acetic acid.

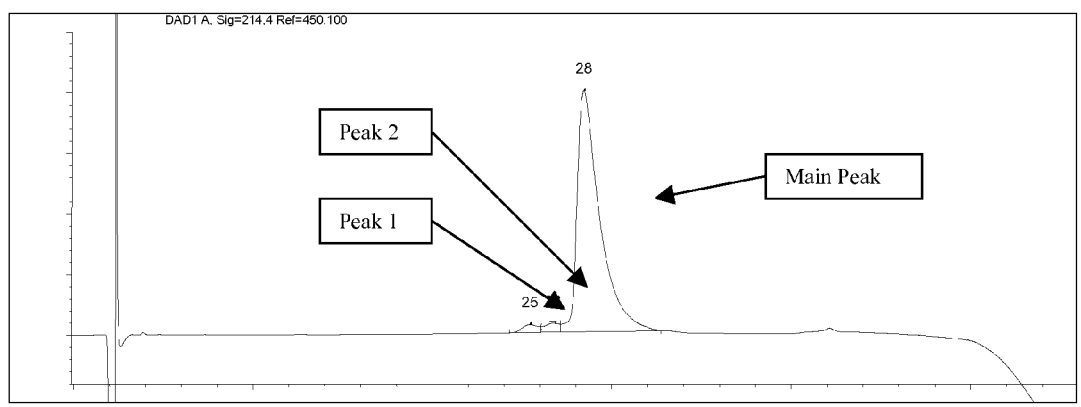
Fig. 5a: rp-HPLC chromatogram of GDF-5 reference standard in 10 mM HCl.

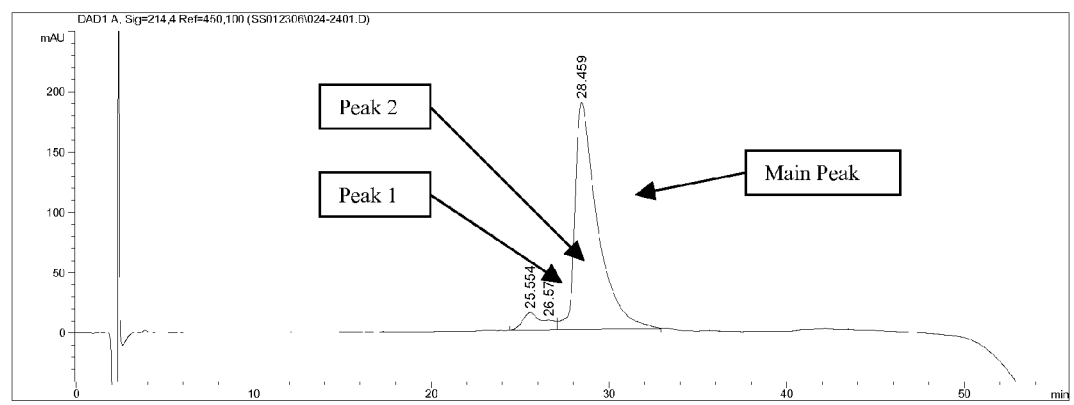
Fig. 5b: rp-HPLC chromatogram of GDF-5 in 10 mM HCl after 5 freeze-thaw cycles.

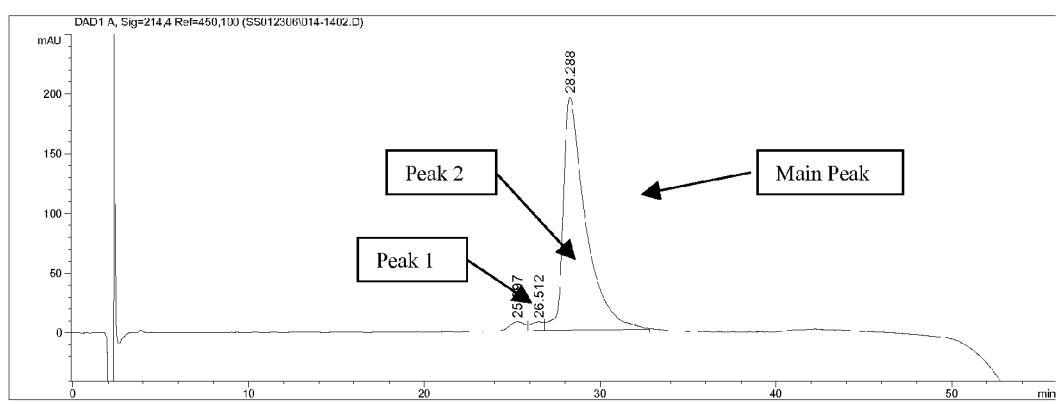
Fig. 5c: rp-HPLC chromatogram of GDF-5 in 50 mM acetic acid after 5 freeze-thaw cycles.

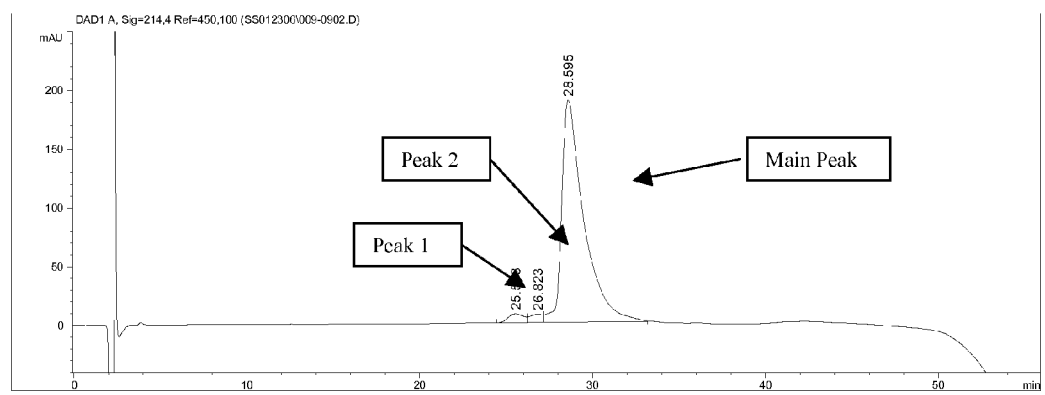
Figure 5d: rp-HPLC chromatogram of GDF-5 in 0.01% TFA after 5 freeze-thaw cycles.

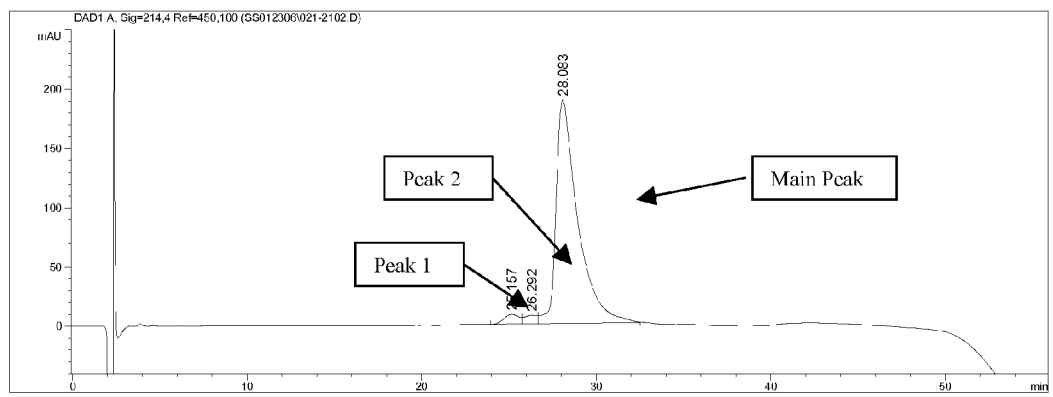
Figure 5e: rp-HPLC chromatogram of GDF-5 in 1 mM HCl after 5 freeze-thaw cycles.

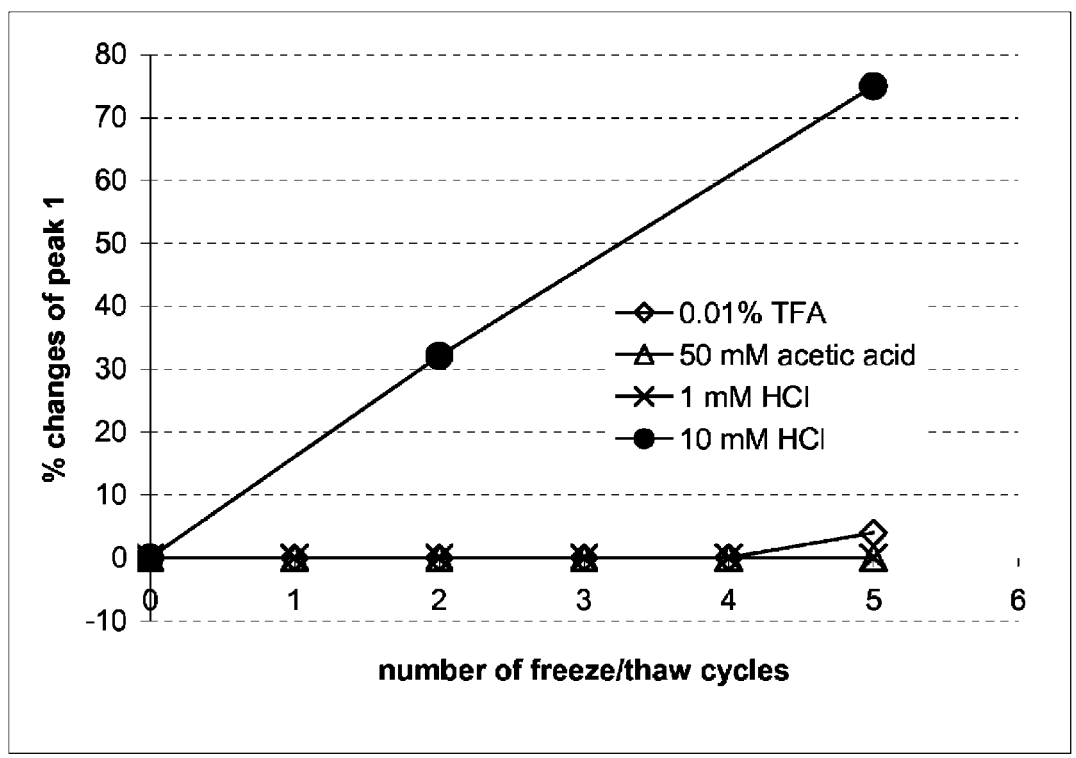
Figure 6: Percentage change in peak 1 after 5 freeze-thaw cycles

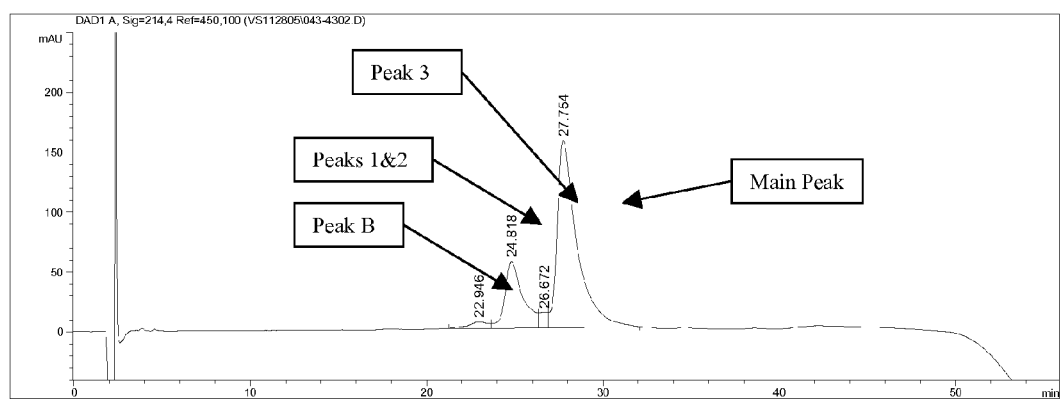
Figure 7: rp-HPLC chromatogram of GDF-5 in 12 mM HCl after 6 days at RT.

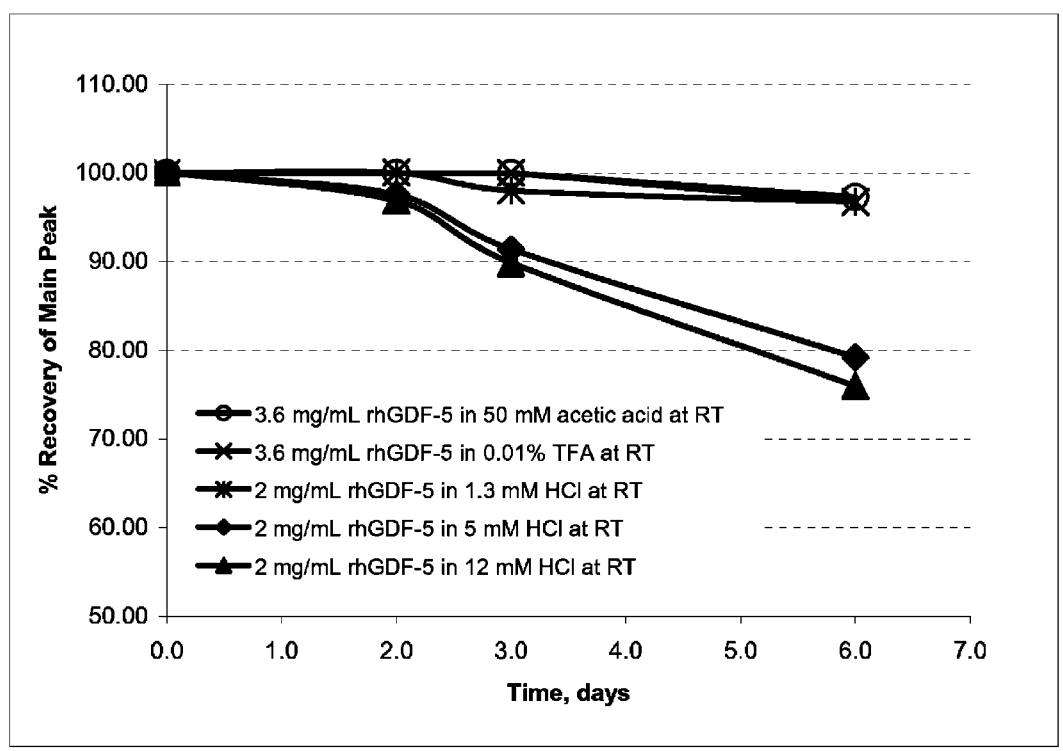
Figure 8: Degradation trends of GDF-5 in different solvents at RT.

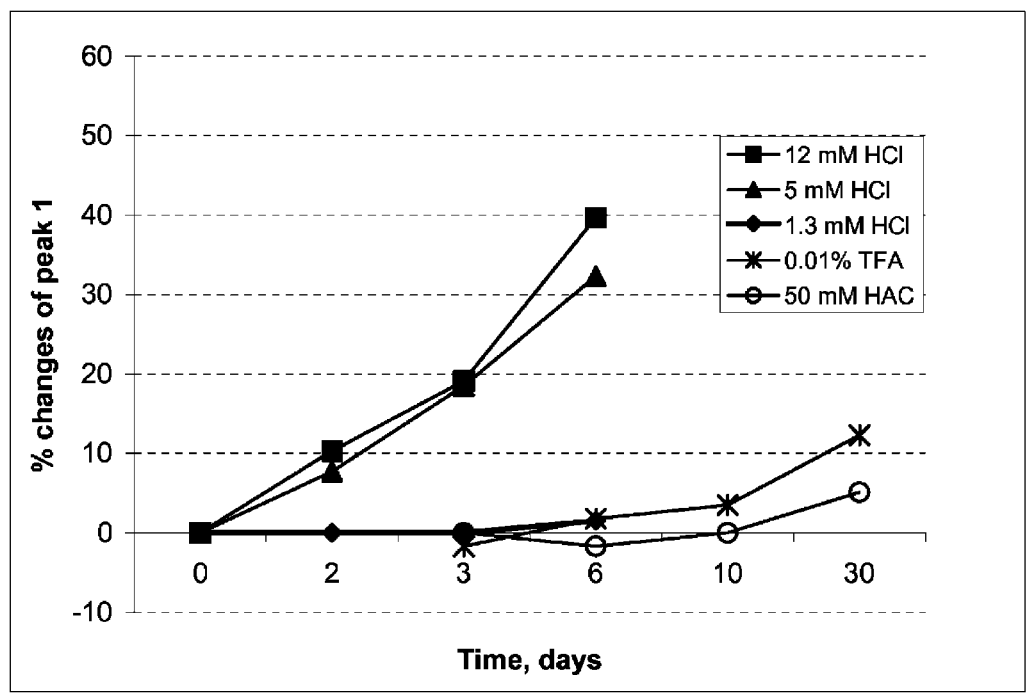
Fig. 9: Degradation trends of GDF-5 in different solvents at 2-8°C.

STABLE COMPOSITION OF GDF-5 AND METHOD OF STORAGE

RELATED APPLICATION

This application claims priority from a provisional filing, U.S. App. Pat. No. 60/954,413 entitled "GDF-5 PROTEIN STORAGE," which was filed on, Aug. 7, 2007.

FIELD OF THE INVENTION

The invention relates to liquid compositions of bone morphogenetic proteins for improved stability during handling and prolonged storage at reduced temperatures. More specifically, the invention relates to biocompatible liquid compositions comprising GDF-5 in an acidic solution having a pH of from about 3.0 to about 3.6, having improved protein stability during handling and prolonged storage at reduced temperatures.

BACKGROUND

GDF-5 is a member of the Bone Morphogenetic Proteins (BMP), which is a subclass of the TGF-β superfamily of proteins. GDF-5 includes several variants and mutants, including mGDF-5 first isolated from the mouse by Lee (U.S. Pat. No. 5,801,014). Other variants include MP52, which is the patented name (WO 95/04819) for the human form of GDF-5, which is also known as hGDF-5 and also as LAP-4 (Triantfilou, et al. *Nature Immunology* 2, 338-345 (2001)); also CDMP-1, an allelic protein variant of hGDF-5 (WO 96/14335); also rhGDF-5, the recombinant human form manufactured in bacteria (EP 0955313); also rhGDF-5-Ala83, a monomeric variant of rhGDF-5; also BMP-14, a collective term for hGDF-5/CDMP-1 like proteins; also Radotermin, the international non-proprietary name designated by the World Health Organization; also HMW MP52's, high molecular weight protein variants of MP52; also C465A, a monomeric version wherein the cysteine residue responsible for the intermolecular cross-link is substituted with alanine; also other active monomers and single amino acid substitution mutants including N445T, L441P, R438L, and R438K. For the purposes of this application the term "GDF-5" is meant to include all variants and mutants of the GDF-5 protein, wherein rhGDF-5 is the exemplary member having 119 amino acids.

All members of the BMP family share common structural features including a carboxy terminal active domain and share a highly conserved pattern of cysteine residues that create three intramolecular disulfide bonds and one intermolecular disulfide bond. The active form can be either a disulfide-bonded homodimer of a single family member or a heterodimer of two different members (see Massague, et al. *Annual Review of Cell Biology* 6:957 (1990); Sampath, et al. *Journal of Biological Chemistry* 265:13198 (1990); Celeste et al. *PNAS* 87:9843-47 (1990); U.S. Pat. No. 5,011,691, and U.S. Pat. No. 5,266,683). The proper folding of the GDF-5 protein and formation of these disulfide bonds are essential to biological functioning, and misfolding leads to inactive aggregates and cleaved fragments.

The production of BMP's from genetically modified bacteria, and of GDF-5 in particular, utilizes plasmid vectors to transform *E. coli* to produce monomer GDF-5 protein in high yield (see for example Hotten U.S. Pat. No. 6,764,994 and Makishima U.S. Pat. No. 7,235,527). The monomer is obtained from inclusion bodies, purified, and refolded into homodimers of GDF-5 protein to produce the biologically active dimer of the GDF-5 protein. The steps leading to the dimer utilize various pharmaceutically unacceptable materials to modify the solubility in order to enable the separation and purification of the GDF-5 protein.

The degradation of proteins in general has been well described in the literature, but the storage and solubility of bone morphogenetic proteins, particularly GDF-5 has not been well described. BMP-2 is readily soluble at concentrations greater than 1 mg/ml when the pH is below 6, and above pH 6 the solubility can be increased by the addition of 1 M NaCl, 30% isopropanol, or 0.1 mM heparin (Ruppert, et al. *Eur J Biochem* 237, 295-302 (1996). GDF-5 is nearly insoluble in physiological pH ranges and buffers and is only soluble in water at extreme pH (Honda, et al. *Journal of Bioscience and Bioengineering* 89(6), 582-589 (2000)). GDF-5 is soluble at an alkaline pH of about 9.5 to 12.0, however proteins degrade quickly under these conditions and thus acidic conditions are used for the preparation of GDF-5 protein.

Biocompatible compositions of the GDF-5 protein present great challenges to obtain reasonable solubility and concurrent stability of the protein. The current method of storage for GDF-5 protein utilizes 10 mM HCl at pH 2 and −80° C. for long-term storage, but even these conditions provide for some degradation of the protein, particularly with repeated freeze-thaw cycles. We performed a trypsin digestion of late eluting species of the GDF-5 protein and found non-tryptic peptide fragments using MALDI-TOF (matrix assisted laser desorption ionization-time of flight mass spectrometry) analysis, indicating acid-catalyzed cleavage of the protein during storage and subsequent aggregation of the fragments. We also separately performed sequential freeze-thaw cycles and prolonged exposure to elevated temperatures of GDF-5 protein solutions. Both of these tests showed degradation of the protein in the current 10 mM HCl storage solvent. Thus there is a need for improved compositions for the handling and storage of GDF-5 protein solutions.

SUMMARY OF THE INVENTION

The present invention provides compositions for the handling and long-term storage of GDF-5 solutions at reduced temperatures that provide for improved stability of the GDF-5 protein. By increasing the pH of the storage solution from 2 to about 3, a significant improvement in the stability of the GDF-5 protein is realized, without adversely affecting the solubility of the protein. Suitable solvent systems include, but are not limited to hydrochloric acid (HCl), acetic acid, trifluoroacetic acid (TFA), and phosphoric acid, in amounts to provide a pH of from about 3.0 to about 3.6.

BRIEF DESCRIPTION OF THE DRAWINGS

FIG. 1 shows SDS-PAGE analysis of various reduced and non-reduced GDF-5 compositions.

FIG. 2 shows circular dichroism analysis of various GDF-5 compositions.

FIG. 3 shows circular dichroism analysis of a stock 10 mM HCl GDF-5 solution further diluted with water.

FIG. 4a shows the DSC spectra of GDF-5 in 10 mM HCl.

FIG. 4b shows the DSC spectra of GDF-5 in 1 mM HCl.

FIG. 4c shows the DSC spectra of GDF-5 in 0.01% (v/v) TFA.

FIG. 4d shows the DSC spectra of GDF-5 in 0.01% (v/v) phosphoric acid.

FIG. 4e shows the DSC spectra of GDF-5 in 0.01% (v/v) acetic acid.

FIG. 5a shows an rp-HPLC chromatogram of a GDF-5 reference standard in 10 mM HCl.

FIG. 5b shows an rp-HPLC chromatogram of GDF-5 in 10 mM HCl after 5 freeze-thaw cycles.

FIG. 5c shows an rp-HPLC chromatogram of GDF-5 in 50 mM acetic acid after 5 freeze-thaw cycles.

FIG. 5d shows an rp-HPLC chromatogram of GDF-5 in 0.01% (v/v) TFA after 5 freeze-thaw cycles.

FIG. 5e shows an rp-HPLC chromatogram of GDF-5 in 1 mM HCl after 5 freeze-thaw cycles.

FIG. 6 shows the percentage change in peak 1 of the various samples shown in FIGS. 5b-e.

FIG. 7 shows an rp-HPLC chromatogram of GDF-5 in 12 mM HCl after 6 days at RT.

FIG. 8 shows degradation trends of GDF-5 in different solvents at RT.

FIG. 9 shows degradation trends of GDF-5 in different solvents at 2-8° C.

DETAILED DESCRIPTION OF THE INVENTION

We investigated the use of a number of different solvent systems in order to improve the stability of GDF-5 protein solutions during handling and storage, and herein describe useful compositions for working with this protein. Since it's discovery and the subsequent development of recombinant human forms, GDF-5 has been stored in a 10 mM HCl solvent system at −80° C. to preserve the protein structure. Partly because of its lack of glycosylation, GDF-5 is less soluble than other BMP's, including BMP-2, for which the bulk of the scientific literature is directed to. There are few reports, if any, available on the solubility and stability of GDF-5. The preparation and isolation of the GDF-5 monomer from plasmid transformed bacteria and the subsequent refolding into dimer presents a different set of issues and problems than the handling and storage of the bioactive dimer. On the other hand, working with the mature dimer GDF-5 protein in biocompatible compositions presents a different set of problems, and the literature yields very little physicochemical information regarding the solubility and stability of the GDF-5 protein.

It is an object of the present invention to provide a composition of GDF-5 protein in a solvent system that provides for improved protein stability during handling and storage. It is another object of the present invention to provide a biocompatible solution of GDF-5 protein that is stable during prolonged storage at reduced temperatures. It is another object of the present invention to provide a biocompatible solution of GDF-5 protein that is stable during handling at room temperature. It is another object of the present invention to provide a method of preserving a solution of GDF-5 protein by providing a solvent system having a pH of from about 3.0 to about 3.6, wherein the GDF-5 protein is stabilized and has reduced susceptibility to acid catalyzed cleavage while still maintaining a useful solubility.

For the purposes of this application definitions of the following terms will be useful. The term "GDF-5" is meant to include all synonyms, variants and mutations of the GDF-5 protein molecule, including, but not limited to GDF-5, mGDF-5, hGDF-5, MP-52, LAP-4, radotermin, CDMP-1, C465A, and rhGDF-5, wherein rhGDF-5 is the exemplary member of the group. The term "GDF-5" is also understood to include monomeric GDF-5 proteins, which have also been shown to be biologically active. The term "room temperature", herein abbreviated as "RT" or "R.T.", is understood to mean the ambient temperature of an ordinary office or laboratory, being from about 18 to about 25° C. The term "bulk", as used herein when referring to "bulk protein" or "bulk solution" is understood to mean a solution of GDF-5 in 10 mM HCl and stored at −80° C. after isolation and purification from the production process, and is equivalent with the terms "stock", "stock protein", and "stock solution".

We undertook several studies of bulk GDF-5 solution to determine the extent of protein degradation and the need for improved solvent systems and conditions for the handling and storage of the GDF-5 protein. We performed MALDI-TOF analysis after performing a trypsin digestion of the late eluting peak (aggregates) from extracts of GDF-5 protein isolated from HEALOS™ mineralized collagen sponges, which were loaded with the GDF-5 protein 10 mM HCl solution and subsequently lyophilized. We observed non-tryptic fragments, indicative of acid-catalyzed cleavage of the GDF-5 protein.

In efforts to discover improved compositions for the handling and storage of GDF-5 we examined the physicochemical properties of the protein in five different solvent environments: 10 mM HCl (the current solvent system for bulk protein), 1 mM HCl, 0.01% (v/v) acetic acid, 0.01% (v/v) TFA, and 0.01% (v/v) phosphoric acid. MALDI-TOF analysis of the GDF-5 protein was done at the Mass Spectrometry Core Facility, Dana-Farber Cancer Institute in Boston, Mass. Samples were mixed with sinapinic acid, spotted and allowed to dry on a stainless steel plate, and then analyzed on a Voyager DE-STR mass spectrometer in linear mode (manufactured by Applied Biosystems, Framingham, Mass.). The percentage aggregate estimated by peak height analysis was found to be about 23.5% in 10 mM HCl as opposed to 8-12% in the remaining four solvents. In this estimation, we assumed any mass greater than 27 kDa to be an aggregate. It should be noted that MALDI is not a quantitative technique, so the absolute percentage of aggregates in each solvent is only an approximation. Nevertheless, the data clearly indicated that there was a greater proportion of aggregates in 10 mM HCl than in the other four solvents.

We performed SDS-PAGE analysis of GDF-5 in the same set of solvent systems. FIG. 1 shows the SDS-PAGE analysis of reduced and non-reduced GDF-5 in the five different solvent environments (10 mM HCl, 1 mM HCl, 0.01% (v/v) TFA, 0.01% (v/v) acetic acid, and 0.01% (v/v) phosphoric acid). In the non-reduced gel, a small amount of aggregate was observed, while in the reduced gel there was clear indication of the presence of low molecular weight species, probably resulting from acid cleavage. No significant difference was noted between the migration profiles of GDF-5 reconstituted in the five different solvent environments.

We also performed far UV circular dichroism (CD) of GDF-5 protein in the same five solvent environments (10 mM HCl, 1 mM HCl, 0.01% (v/v) TFA, 0.01% (v/v) acetic acid, and 0.01% (v/v) phosphoric acid). The results are shown in FIG. 2 as an overlay plot, and demonstrate a unique CD spectrum for GDF-5 in 10 mM HCl, distinctly different from the spectra in the other solvents. No significant difference in the secondary structural distribution of GDF-5 was noted when the remaining four solvent environments were compared to each other. In another experiment, bulk GDF-5 solution (3.8 mg/mL in 10 mM HCl) was diluted with water to achieve a desired protein concentration of 0.2 mg/mL while increasing the pH (through dilution), and then the CD analysis was done using water as a blank. The spectrum is shown in FIG. 3 and clearly demonstrates a subtle pH-dependent structural change in GDF-5. At pH 3, the GDF-5 protein becomes relatively more structured, with less random and more Beta contribution, than the spectrum at lower pH.

We performed Differential Scanning Calorimetry (DSC) on GDF-5 protein in the same five solvent environments (10 mM HCl, 1 mM HCl, 0.01% (v/v) acetic acid, 0.01% (v/v) TFA, and 0.01% (v/v) phosphoric acid). FIGS. 4a through 4e show the DSC thermal data of the samples after instrument baseline and solvent subtraction and concentration normalization. Bulk GDF-5 in 10 mM HCl (FIG. 4a) shows a weak thermal transition with $T_m<30°$ C. and also a broad weak transition near 65° C. The heat transfer was significantly poor. In contrast, GDF-5 protein dialyzed against 1 mM HCl (FIG. 4b), 0.01% (v/v) TFA (FIG. 4c), and 0.01% (v/v) phosphoric acid (FIG. 4d), showed a large transition near 40° C. and a smaller endothermic transition near 85° C. In 0.01% (v/v) acetic acid (FIG. 4e), the results showed a significant increase in both transitions: $T_{M1}\sim60°$ C. and $T_{M2}\sim94°$ C. The thermodynamic parameters, namely ΔH and ΔS values were also significantly higher in 0.01% (v/v) acetic acid. This result suggests that the GDF-5 protein's thermal stability is much greater in an acetic acid environment or at a higher pH. In an earlier study, we noted that the C465A monomer, which cannot form an intermolecular disulfide bridge, did not exhibit the first endotherm near 40° C., suggesting that this transition represents disulfide interaction between the two monomer units.

In another set of experiments we have shown that even as few as two freeze-thaw cycles of GDF-5 in 10 mM HCl can lead to a substantial increase in fragments and degradation products, as shown by rp-HPLC. FIG. 5a shows an rp-HPLC chromatogram of a reference standard of bulk GDF-5, showing good purity and very little additional peaks. FIG. 5b shows an rp-HPLC chromatogram of bulk GDF-5 after 5 freeze-thaw cycles, showing an increase in the fragments appearing as additional peaks (peak 1 & peak 2). FIG. 5c shows an rp-HPLC chromatogram of GDF-5 in 50 mM acetic acid after 5 freeze-thaw cycles, showing little, if any, increase in the fragments appearing as additional peaks (peak 1 & peak 2). FIG. 5d shows an rp-HPLC chromatogram of GDF-5 in 0.01% (v/v) TFA after 5 freeze-thaw cycles, showing little, if any, increase in the fragments appearing as additional peaks (peak 1 & peak 2). FIG. 5e shows an rp-HPLC chromatogram of GDF-5 in 1 mM HCl after 5 freeze-thaw cycles, showing little, if any, increase in the fragments appearing as additional peaks (peak 1 & peak 2).

FIG. 6 shows a plot directly comparing only the changes in peak 1, and shows approximately a 30% increase in the peak 1 of the GDF-5 protein in 10 mM HCl sample after only 2 freeze-thaw cycles, whereas the other solvent systems show minimal changes to peak 1 after 5 freeze-thaw cycles. After 5 freeze-thaw cycles the percent change in peak 1 for the bulk 10 mM HCl solution was approximately 75%, whereas the other solvent systems showed very little change in peak 1.

In another group of experiments we investigated the potential of various solvent systems to provide improved stability to liquid GDF-5 protein solutions at temperatures of 2-8° C. and at room temperature (RT, approximately 25° C.). In these experiments the stability of GDF-5 protein was evaluated by rp-HPLC in the following solvent systems: 1.3 mM HCl, 5 mM HCl, 12 mM HCl, 0.01% (v/v) TFA, and 50 mM acetic acid. Samples of the GDF-5 protein solutions were prepared by dialysis with the selected solvents at 2-8° C. overnight and transferred as aliquots into small vials at about 1 mL/vial and placed accordingly at 2-8° C. or at room temperature. At each designated time point, one vial from each set was removed and stored at −80° C. until the analysis was performed. The results show that GDF-5 was stable in both 50 mM acetic acid (pH 3.3) and 0.01% (v/v) TFA (pH 3.3) solutions at room temperature after three days and in 1.3 mM HCl (pH 3.3) after 2 days, while it was not stable at room temperature in either 5 mM HCl (pH 2.5) or 12 mM HCl (pH 2.1) after 2 days (see FIGS. 7 and 8).

At 2-8° C., the GDF-5 protein was stable for at least 30 days in 50 mM acetic acid or 0.01% (v/v) TFA solution, and stable for at least 6 days in 1.3 mM HCl. In contrast, the GDF-5 protein was degraded in 5 mM HCl and 12 mM HCl solutions at 2-8° C., and formed degradation species after 2 days as evidenced by rp-HPLC (see FIG. 9).

The following examples are meant only to be illustrative in nature of the present invention, and not to be limiting in scope. One skilled in the art would easily conceive of other embodiments that would be considered within the scope of the present invention.

Example 1

Four different solvent systems, 1 mM HCl, 0.01% (v/v) acetic acid, 0.01% (v/v) TFA, and 0.01% (v/v) phosphoric acid, were tested for their ability to provide improved GDF-5 protein stability over the standard 10 mM HCl solvent system currently used. Approximately 1-2 ml of bulk GDF-5 protein (3.8 mg/ml) in 10 mM HCl was taken from a freshly thawed sample and dialyzed for 24 hours at 2-8° C. with 3 changes each of 1 liter of test solution to produce a GDF-5 protein solution in each of the four different solvent systems. The concentration of the dialysates was determined from the absorbance value at 280 nm using an extinction coefficient of 1.16 for a 1 mg/ml solution and a pathlength of 1 cm. The GDF-5 protein solutions were then analyzed by SDS-PAGE, Circular Dichroism (CD), Differential Scanning Calorimetry (DSC), and MALDI-TOF.

SDS-PAGE

The GDF-5 protein samples were diluted in Bio-Rad 8-16% gradient gel appropriate sample buffer (provided by the manufacturer) either with (reduced) or without (non-reduced) 50 mM dithiothreitol (DTT). The samples were denatured by heating at 90° C. for 5 min and then centrifuged briefly at 5000 rpm. Electrophoresis was carried out at 200 volts constant for 1 hour on an 8-16% Bio-Rad criterion gel with 1× tris-glycine-SDS running buffer. Gels were incubated in 100 mL 10% methanol, 7% acetic acid (Ruby fix/destain solution) for 1 hour on an orbital shaker at 45 rpm. The fix solution was decanted and 80 mL Sypro-Ruby (Bio-Rad) was added. Gels were incubated overnight in the dark on an orbital shaker at 45 rpm. The Sypro-Ruby was decanted and 100 mL destain solution was added. Gels were incubated for 3 hours on an orbital shaker at 45 rpm. Finally, gels were imaged on a Bio-Rad Gel Doc imager.

In the non-reduced gels, a small amount of aggregate was observed, while in the reduced gels there was clear indication of the presence of low molecular weight species, probably resulting from acid cleavage. No significant difference was noted between the migration profiles of GDF-5 reconstituted in the five different solvent environments.

Circular Dichroism

Circular Dichroism was carried out on an AVIV Model 60DS Circular Dichroism Spectropolarimeter. For each sample, scans were taken between 190 and 250 nm. For each scan, data were collected at 1 nm intervals for 2 sec at each interval. The scan temperature was 23° C. The final protein concentration was 0.2 mg/mL. Data represented the average of three scans. A buffer blank was also recorded under identical conditions and the CD spectrum of the buffer blank was subtracted from that of the sample. All runs were made using 0.01% TFA as a blank. Cuvettes had a path length of 1 mm.

The scans were normalized using Mean residue weight (a value of 115) and inserting it into the equation:

$$[\theta]=[0.1 \times R_{residue}]/[\text{conc. (mg/mol)} \times \text{light path}].$$

The value of $[\theta]$ was calculated at each wavelength to give mean residue ellipticities. Finally, an estimate of secondary structure was determined using the program PROSEC v.2.1 (copyright 1987 by AVIV Associates).

Differential Scanning Calorimetry

FIGS. 4a through 4e show DSC thermal data for the GDF-5 protein in the five different solvent environments, after instrument baseline and solvent subtraction and concentration normalization. The samples were stored at −80° C.; thawed and degassed under vacuum with stirring for 8 minutes at room temperature prior to loading in the DSC cell and scanned in duplicate at 60° C./hr from 5-100° C. on a MicroCal VP-DSC. The protein concentration was 0.51 mg/mL for all samples. Bulk GDF-5 in 10 mM HCl shows a weak thermal transition with $T_m < 30°$ C. and a broad weak transition near 65° C. The heat transfer was significantly poor. In contrast, protein dialyzed against 1 mM HCl, 0.01% TFA and 0.01% phosphoric acid showed a large transition near 40° C. and a smaller endothermic transition near 85° C. In 0.01% acetic acid, the results showed a significant increase in both transitions: $T_{M1} \sim 60°$ C. and $T_{M2} \sim 94°$ C. The thermodynamic parameters, namely $\Delta H$ and $\Delta S$ values were also significantly higher in the 0.01% acetic acid sample. This result suggests that the protein's thermal stability is much greater in an acetic acid environment or at a higher pH. We noted in an earlier study that the C465A monomer, which cannot form an intermolecular disulfide bridge, did not exhibit the first endotherm near 40° C., suggesting that this transition represents disulfide interaction between the two monomer units.

MALDI-TOF:

MALDI-TOF analysis of intact protein in five different solvent environments was done at the Mass Spectrometry Core Facility, Dana-Farber Cancer Institute in Boston, Mass. Samples were mixed with sinapinic acid, spotted and allowed to dry on a stainless steel plate, and then analyzed on a Voyager DE-STR mass spectrometer in linear mode (manufactured by Applied Biosystems, Framingham, Mass.). No significant difference was noted in the weight average molecular weight of the major dimer as well as the other higher oligomer species in any of these solvents. All five spectra had their 27 kDa peak normalized to 100% relative intensity. The percentage aggregate estimated by peak height analysis was found to be about 23.5% in 10 mM HCl as opposed to 8-12% in the remaining four solvents. In this estimation, we assumed any mass>27 kDa to be an aggregate. It should be noted that MALDI is not a quantitative technique, so the absolute percentage of aggregates in each solvent is only an approximation. Nevertheless, the data clearly indicate that there is a greater proportion of aggregates in 10 mM HCl than in the other four solvents.

Overall, the combined results showed that in each of the four different solvent systems tested GDF-5 protein had good linearity in serial dilution and exhibited improved stability over the 10 mM HCl composition.

Example 2

An attempt was made to assess solubility of GDF-5 in 20 mM acetic acid. Stock GDF-5 in 10 mM HCl (3.8 mg/mL) was dialyzed against 20 mM acetic acid with a 3,500 MW cut off membrane, then lyophilized, and finally, the dried mass was reconstituted in 20 mM acetic acid. The OD at 280 nm was determined. It was noted that a clear solution was readily obtained with 6.5 mg/mL GDF-5 in 20 mM acetic acid. In a separate attempt the GDF-5 protein in 20 mM acetic acid was lyophilized and then reconstituted in 1 mM HCl. Again, the OD at 280 nm was determined and the results indicated that a clear solution could be readily obtained with a GDF-5 protein concentration of 6.5 mg/mL.

Example 3

The stability of GDF-5 protein was evaluated through five freeze/thaw cycles in different storage solvents, including 1 mM HCl, 10 mM HCl, 0.01% (v/v) TFA, and 50 mM acetic acid. Bulk GDF-5 in 10 mM HCl was removed from −80° C. and thawed at 2-8° C. The GDF-5 protein solution was then dialyzed with the selected solvents at 2-8° C. overnight (dialysis cassettes: Pierce, Cat #66380, 10000 MWCO). The dialyzed samples were transferred into small vials at about 1 mL/vial and placed at −80° C. In each freeze/thaw cycle, the test samples were frozen at −80° C. for at least 19 hours and thawed at room temperature for at least 5 hours. At the end of each cycle one vial of each solvent sample was removed and stored at −80° C. prior to analysis so that all the samples were analyzed at same time for visual appearance, rp-HPLC, UV spectroscopy, and pH.

The test samples in glass vials were checked for clarity and particles. The sample vials were inspected using a vertical light against a black background. The clarity of the test samples was compared with a pure water sample. All samples appeared clear and transparent; the GDF-5 protein was still soluble at the concentration of 3.6 mg/mL after the five-freeze/thaw cycles.

A non-reduced rp-HPLC method was used to monitor GDF-5 protein contents and degradation species. Briefly, the test samples were diluted with 1 mM HCl to 0.1 mg GDF-5/mL and the diluted sample (50 µl) was directly injected onto the HPLC column (Vydac 218TP52, C18 column) which was eluted with 0.15% (v/v) TFA in water and 0.15% (v/v) TFA in acetonitrile as the mobile phase. The eluted peaks were monitored at 214 nm. The peak areas were compared to reference standard areas to determine the GDF-5 protein content. The percentage of each peak area was calculated to monitor the changes of the main peak and minor peaks (degradation peaks).

Representative chromatograms are shown in FIGS. 5a-e. The main peak of GDF-5 and other degradation peaks are indicated in the figures. No significant changes in protein concentration were observed in the samples under all storage conditions. The GDF-5 protein was stable with 100% main peak recovery after five freeze/thaw cycles in 1 mM HCl, 50 mM acetic acid, and 0.01% (v/v) TFA solution. However, GDF-5 was less stable in the 10 mM HCl solution, as peak 1 increased dramatically after the second freeze/thaw cycle (see FIG. 6).

The protein content was also determined by UV spectroscopy. The test samples were diluted with an appropriate solvent prior to analysis. The concentration of GDF-5 was calculated using an extinction coefficient of 1.16 mL/mg*cm at 280 nm. UV results indicate that there was no significant change in protein concentration in all samples during the course of study. The protein concentrations as determined by UV spectroscopy and HPLC were similar. The pH of the samples was measured directly using a calibrated pH meter without dilution. The pH of all samples was stable and the storage conditions did not shift the pH.

The results show that GDF-5 was stable after 5 freeze/thaw cycles in 1 mM HCl, 50 mM acetic acid, and 0.01% (v/v) TFA solutions. In contrast, GDF-5 was less stable in 10 mM HCl solution and degradation species started forming after the second freeze/thaw cycle.

Example 4

In this example the stability of GDF-5 protein was evaluated in various acidic solvents including 1.3 mM HCl, 5 mM HCl, 12 mM HCl, 0.01% (v/v) TFA, and 50 mM acetic acid for prolonged exposure to temperatures of 2-8° C. and also at room temperature (approximately 25° C.). Bulk GDF-5 in 10 mM HCl was removed from −80° C. and thawed at 2-8° C. The GDF-5 protein solution was then dialyzed with the selected solvents at 2-8° C. overnight (dialysis cassettes: Pierce, Cat #66380, 10000 MWCO). The dialyzed samples were transferred as aliquots into small vials at about 1 mL/vial and placed accordingly at 2-8° C. or room temperature. At each designated time point, one vial from each set was removed and stored at −80° C. until the analysis was performed using rp-HPLC, UV spectroscopy, and pH meter.

The results show that GDF-5 was stable in both 50 mM acetic acid (pH 3.3) and 0.01% (v/v) TFA (pH 3.3) solutions at room temperature for three days and in 1.3 mM HCl (pH 3.3) for 2 days, while it was not stable at room temperature in either 5 mM HCl (pH 2.5) or 12 mM HCl (pH 2.1). At 2-8° C., GDF-5 protein was stable for at least 30 days in 50 mM acetic acid or 0.01% (v/v) TFA solution, and stable for at least 6 days in 1.3 mM HCl. In contrast, GDF-5 was rapidly degraded in 5 mM HCl as well as in 12 mM HCl solutions at 2-8° C., forming degradation species within 6 days as evidenced on HPLC (see FIG. 9). The studies using HCl were terminated at 6 days.

Although this invention has been described with reference to specific embodiments, variations and modifications of the methods and means for increasing the pH of a solution of GDF-5 protein will be readily apparent to those skilled in the art. Such variations and modifications are intended to fall within the scope of the appended claims.

We claim:

1. A stable composition consisting of GDF-5 and a biocompatible acid in an aqueous acidic solution having a pH of from about 3.0 to about 3.6, wherein the biocompatible acid is acetic acid present in an amount of about 20 to about 50 mM.

2. The composition of claim 1 wherein the pH is from about 3.2 to about 3.4.

3. A method of stabilizing a solution of GDF-5 protein comprising the steps of:
   a. Providing a sample of GDF-5 and a biocompatible acid in an aqueous acidic solution having a pH of from about 3.0 to about 3.6, wherein the biocompatible acid is acetic acid present in an amount of about 20 to about 50 mM and
   b. Cooling said solution of GDF-5 to a temperature of about 2° to about 8° C.

4. The method of claim 3, wherein the solution is further cooled to about −20° C.

5. The method of claim 3, wherein the solution is further cooled to about −80° C.

6. The composition of claim 1 wherein the GDF-5 is rhGDF-5.

* * * * *